(12) United States Patent
Kangas et al.

(10) Patent No.: US 12,575,750 B2
(45) Date of Patent: Mar. 17, 2026

(54) ASYMMETRIC SENSORS FOR RING WEARABLE

(71) Applicant: Oura Health Oy, Oulu (FI)

(72) Inventors: Mika Petteri Kangas, Oulu (FI);
Jukka-Tapani Mäkinen, Oulu (FI);
Jaakko Tapio Vartiainen, Oulu (FI);
Olli Petteri Heikkinen, Oulu (FI);
Kirsi Marja Maansaari, Oulu (FI)

( * ) Notice: Subject to any disclaimer, the term of this
patent is extended or adjusted under 35
U.S.C. 154(b) by 142 days.

(21) Appl. No.: 17/855,283

(22) Filed: Jun. 30, 2022

(65) Prior Publication Data

US 2024/0000328 A1 Jan. 4, 2024

(51) Int. Cl.
*A61B 5/024* (2006.01)
*A61B 5/00* (2006.01)
*G06F 1/16* (2006.01)

(52) U.S. Cl.
CPC ...... *A61B 5/02427* (2013.01); *A61B 5/02438*
(2013.01); *A61B 5/6802* (2013.01); *G06F
1/163* (2013.01)

(58) Field of Classification Search
CPC ............ A61B 5/02427; A61B 5/02438; A61B
5/6802; A61B 5/14552; A61B 5/681;
A61B 5/6824; G06F 1/163
See application file for complete search history.

(56) References Cited

U.S. PATENT DOCUMENTS

| | | | | |
|---|---|---|---|---|
| 2016/0249839 A1* | 9/2016 | Wong | ................... | A61B 5/6817 |
| | | | | 600/323 |
| 2017/0164878 A1* | 6/2017 | Connor | ................. | G09B 19/00 |
| 2020/0000345 A1* | 1/2020 | Connor | ............. | A61B 5/14532 |
| 2023/0320604 A1* | 10/2023 | Cai | .................... | A61B 5/02427 |
| | | | | 600/479 |

* cited by examiner

*Primary Examiner* — Anh Tuan T Nguyen
*Assistant Examiner* — Dean N Edun
(74) *Attorney, Agent, or Firm* — Holland & Hart LLP

(57) ABSTRACT

Methods, systems, and devices for wearable device are
described. A wearable device may include a first light-
emitting component positioned within an inner circumfer-
ential surface of the wearable device at a first radial position
and a second light-emitting component positioned within the
inner circumferential surface of the wearable device at a
second radial position, where the first radial position and the
second radial position define a segment of the inner circum-
ferential surface between the first radial position and the
second radial position. Additionally, the wearable device
may include a photodetector configured to receive light
emitted by the first light-emitting component and the second
light-emitting component. In some cases, the photodetector
may be positioned at a third radial position within the
segment of the inner circumferential surface between the
first radial position and the second radial position, where the
third radial position is offset from a radial midpoint of the
segment.

17 Claims, 8 Drawing Sheets

ASYMMETRIC SENSORS FOR RING WEARABLE

FIELD OF TECHNOLOGY

The following relates to wearable devices and data processing, including asymmetric sensor configurations for wearable devices.

BACKGROUND

Some wearable devices may be configured to collect data from users. For example, a wearable device may include one or more sensors that collect physiological data from a user. Some systems associated with the wearable devices may also be able to perform various actions, such as providing certain health insights to users.

DETAILED DESCRIPTION

Figure 1:
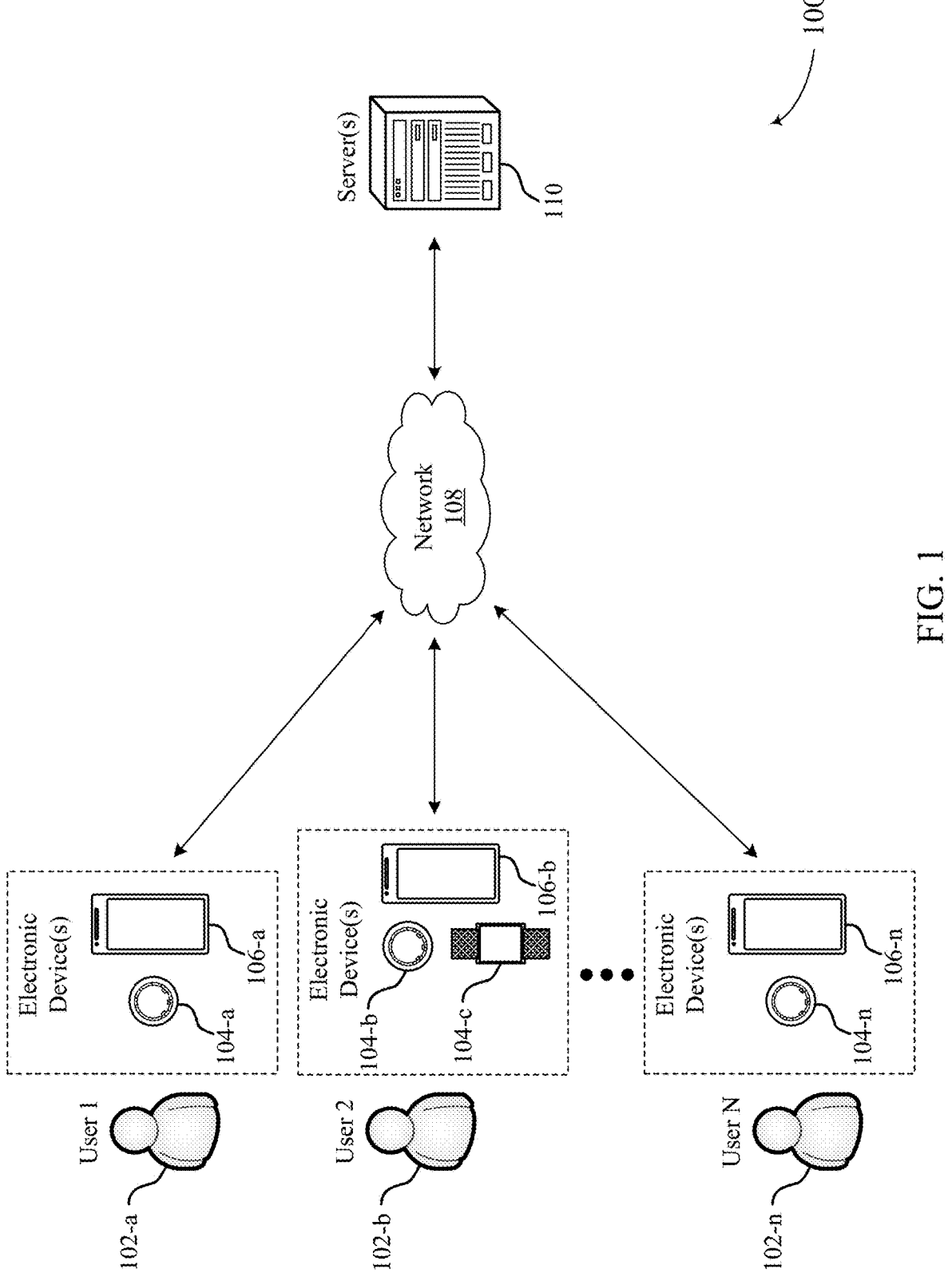
FIG. 1 illustrates an example of a system that supports asymmetric sensor configurations for wearable devices in accordance with aspects of the present disclosure.

Wearable devices, such as a wearable ring device, may be used to collect, monitor, and track physiological data associated with a user based on sensor measurements performed by the wearable device. Examples of physiological data may include temperature data, heart rate data, photoplethysmography (PPG) data, blood-oxygen saturation data, and the like. The physiological data collected, monitored, and tracked via the wearable device may be used to gain health insights about the user, such as the user's sleeping patterns, activity patterns, and the like.

Many wearable devices exhibit symmetrical sensor designs in which the various sensors of the wearable devices are arranged symmetrically with respect to the wearable device. In some cases, wearable devices may exhibit symmetrical sensor designs for aesthetic purposes, or to physical constraints of the wearable device. However, in the context of wearable devices, symmetrical sensor designs may result in negative impacts to the accuracy of some physiological data collected by the wearable device due to biological variations of the user.

For example, a wearable device designed to be worn on a finger of a user may include a set of sensors (e.g., light-emitting diodes (LEDs) and photodetectors). In this example, the set of sensors may be configured to perform various types of measurements, such as heart rate measurements and blood oxygen saturation measurements. In some cases, the set of sensors may be arranged symmetrically around the wearable device so that the set of sensors may accurately collect physiological data associated with a heart rate of the user based on pulsating blood vessels within the finger of the user. However, the pulsating blood vessels may cause veins and arteries in the finger of the user to change size, which may detrimentally affect the ability of the sensor to perform blood oxygen saturation measurements. In other words, the pulsating blood vessels may be used to perform the heart rate measurements, but may be perceived as noise that detrimentally affect the blood oxygen saturation measurements.

In this regard, there is a tension between heart rate measurements and blood oxygen saturation measurements caused by the symmetrical arrangement of the sensors within the wearable device and the physiology of the user's finger. In particular, the symmetrical arrangement of the sensors within the wearable device may result in optimal heart rate measurements, but may detrimentally affect blood oxygen measurements. Conversely, the set of sensors may be arranged within the wearable device in a different symmetrical arrangement that may result in optimal blood oxygen saturation measurements, but may detrimentally affect heart rate measurements.

One solution to this tension between different types of physiological measurements may include utilizing different sets of sensors for different types of measurements (e.g., first set of sensors for heart rate measurements, second set of sensors for blood oxygen measurements). However, additional hardware may render wearable devices too bulky for many users, and may make the wearable devices prohibitively expensive. Moreover, additional sensors within a wearable device may increase power consumption, leading to shorter battery lives.

Accordingly, aspects of the present disclosure support an asymmetrical sensor design for wearable devices which may result in noise reduction and an increase in the accuracy of physiological data collection associated with blood oxygen saturation, among other data. In particular, aspects of the present disclosure may support wearable devices that exhibit some degree of curvature (e.g., curved profile) and that include an asymmetrical sensor design in which at least one sensor (e.g., at least one photodetector) is arranged asymmetrically within the wearable device relative to the other sensors of the wearable device. Such wearable devices that exhibit some degree of curvature may include, but are not limited to, wearable ring devices, wearable necklace devices, wearable bracelet devices, wearable anklet devices, and the like.

For example, a wearable device (e.g., wearable ring device) may support a set of light-emitting components, including a first light-emitting component and a second light-emitting component, located on an inner surface of a wearable device. Additionally, the wearable device may support one or more photodetectors located on the inner surface, including a first photodetector located between the first light-emitting component and the second light-emitting component, where the first photodetector is offset from a midpoint between the first light-emitting component and the second light-emitting component. That is, the first photodetector may be located closer to the first light-emitting component or the second light-emitting component, such that a first optical path between the first photodetector and the first light-emitting component is different in length than a second optical path between the first photodetector and the second light-emitting component. In this regard, the first photodetector may be said to be positioned asymmetrically within the wearable device.

In some implementations, the asymmetrical sensor arrangement of the wearable device described herein may resolve the inherent tension between different types of physiological measurements performed by other wearable devices that exhibit symmetrical sensor arrangements. In particular, the asymmetrical sensor arrangement described herein may enable different pairs of sensors (e.g., pairs of light-emitting components and photodetectors) to exhibit varying optical path lengths with different penetration depths. As such, by enabling different optical path lengths with different penetration depths, the asymmetrical sensor arrangements described herein may use the same set of sensors to perform different types of measurements (e.g., heart rate measurements, blood oxygen measurements) with optical paths of varying lengths and penetration depths, thereby preventing the tension between different types of measurements that may be caused by some symmetrical sensor arrangements.

In some cases, each of the first light-emitting component, the second light-emitting component, and the first photodetector may be associated with one or more apertures, where a respective aperture is offset from a radial midpoint of the associated component (e.g., the first light-emitting component, the second light-emitting component, or the first photodetector). Stated differently, in some cases, the sensors of the wearable ring device may include apertures, where the apertures are offset (e.g., positioned asymmetrically) within the wearable device based on the asymmetrical arrangement of the sensors.

In some cases, a controller associated with the first light-emitting component, the second light-emitting component, the first photodetector, or any combination thereof, may selectively activate the first light-emitting component, the second light-emitting component, or both, based on a respective signal quality or respective power consumption associated with the first light-emitting component, the second light-emitting component, or both. In other words, the controller may be configured to select which optical paths will be used for different types of measurements, where the different optical paths exhibit different optical lengths (e.g., different penetration depths) based on the asymmetrical arrangement of the sensors within the wearable device.

For example, the wearable device may collect physiological data associated with a blood oxygen saturation of a user associated with the wearable device using the first light-emitting component and the photodetector (e.g., the first optical path). However, a system associated with the wearable device may detect a change in signal quality associated with light received by the photodetector from the first light-emitting component, such that the signal quality drops below a threshold signal quality. In such cases, the controller may selectively activate the second light-emitting component and deactivate the first light-emitting diode, such that the wearable device may collect the physiological data associated with the blood oxygen saturation of the user using the second light-emitting component and the photodetector (e.g., the second optical path) based on a signal quality associated with light received by the photodetector from the second light-emitting component failing to exceed the threshold signal quality or based on a comparison of the signal quality associated with light received by the photodetector from the second light-emitting component to a signal quality associated with light received by the photodetector from the first light-emitting component.

Aspects of the disclosure are initially described in the context of systems supporting physiological data collection from users via wearable devices. Aspects of the disclosure are then described in the context of a wearable device and sensor layout. Aspects of the disclosure are further illustrated by and described with reference to apparatus diagrams, system diagrams, and flowcharts that relate to asymmetric sensor configurations for wearable devices, including wearable devices that exhibit some degree of curvature (e.g., curved profile), such as wearable ring devices, wearable necklace devices, wearable bracelet devices, wearable anklet devices, wearable arm/leg band devices, chest straps, headbands, earring devices, and the like.

FIG. 1 illustrates an example of a system 100 that supports asymmetric sensor configurations for wearable devices in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a machine learning classifier, where the machine learning classifier is configured to determine periods of time that the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support asymmetric sensor configurations for wearable devices. In particular, a ring 104, such as a ring 104-a, a ring 104-b, or a ring 104-n, may support multiple sensors in which one or more sensors, such as a photodetector, may be located at an offset from a radial midpoint of a segment created by a set of sensors, such as a first light-emitting component and a second light-emitting component. In other words, a ring 104 may exhibit an asymmetrical sensor arrangement in which at least one sensor of the ring 104 is positioned asymmetrically relative to a hemisphere of the ring 104, relative to other sensors of the ring 104, or both.

For example, a ring 104-a may include a housing configured to contain a photodetector, a first light-emitting component, and a second light-emitting component. The first light-emitting component may be located at a first radial position within an inner circumference of the ring 104-a and the second light-emitting component may be located at a second radial position within the inner circumference of the ring 104-a, such that the first radial position and the second radial position form a segment of the inner circumference with a radial midpoint. Additionally, the photodetector may be located at a third radial position within the inner circumference of the ring 104-a that is offset from the radial midpoint, producing an asymmetric sensor configuration (e.g., the photodetector is arranged asymmetrically with respect to the first and second light-emitting components).

In some cases, locating the photodetector at the third radial position, offset from the radial midpoint, may result in the ring 104-a supporting multiple optical paths of different lengths. That is, a first optical path between the first light-emitting component and the photodetector may be different in length than a second optical path between the second light-emitting component and the photodetector. In such cases, the first optical path may support a first penetration depth into a tissue of the user 102-*a* and the second optical path may support a second penetration depth into the tissue of the user 102-*a*. Thus, a controller associated with the ring 104-*a* may selectively activate the first light-emitting component, the second light-emitting component, or both, based on a desired optical path and/or penetration depth. In some cases, the desired optical path may be based on a signal quality metric associated with each optical path, a power consumption associated with each light-emitting component, or both.

Additionally, each of the first light-emitting component, the second light-emitting component, and the photodetector may be associated with a respective aperture located within an inner circumference surface of the ring 104-*a* housing. For example, the first light-emitting component may be associated with a first aperture, the second light-emitting component may be associated with a second aperture, and the photodetector may be associated with a third aperture. In some cases, each aperture may be offset from a respective sensor. That is, the first aperture may be offset from the first light-emitting diode according to a first radial offset, the second aperture may be offset from the second light-emitting diode according to a second radial offset, and the third aperture may be offset from the photodetector according to a third radial offset. In some cases, the first radial offset, the second radial offset, or both, may be based on the third radial offset. Locating apertures according to radial offsets from respective sensors may enable rings 104 to maintain accurate physiological data collection regardless of a circumference of the rings 104 (e.g., aperture placement may be optimized for a range of ring 104-*a* sizes).

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
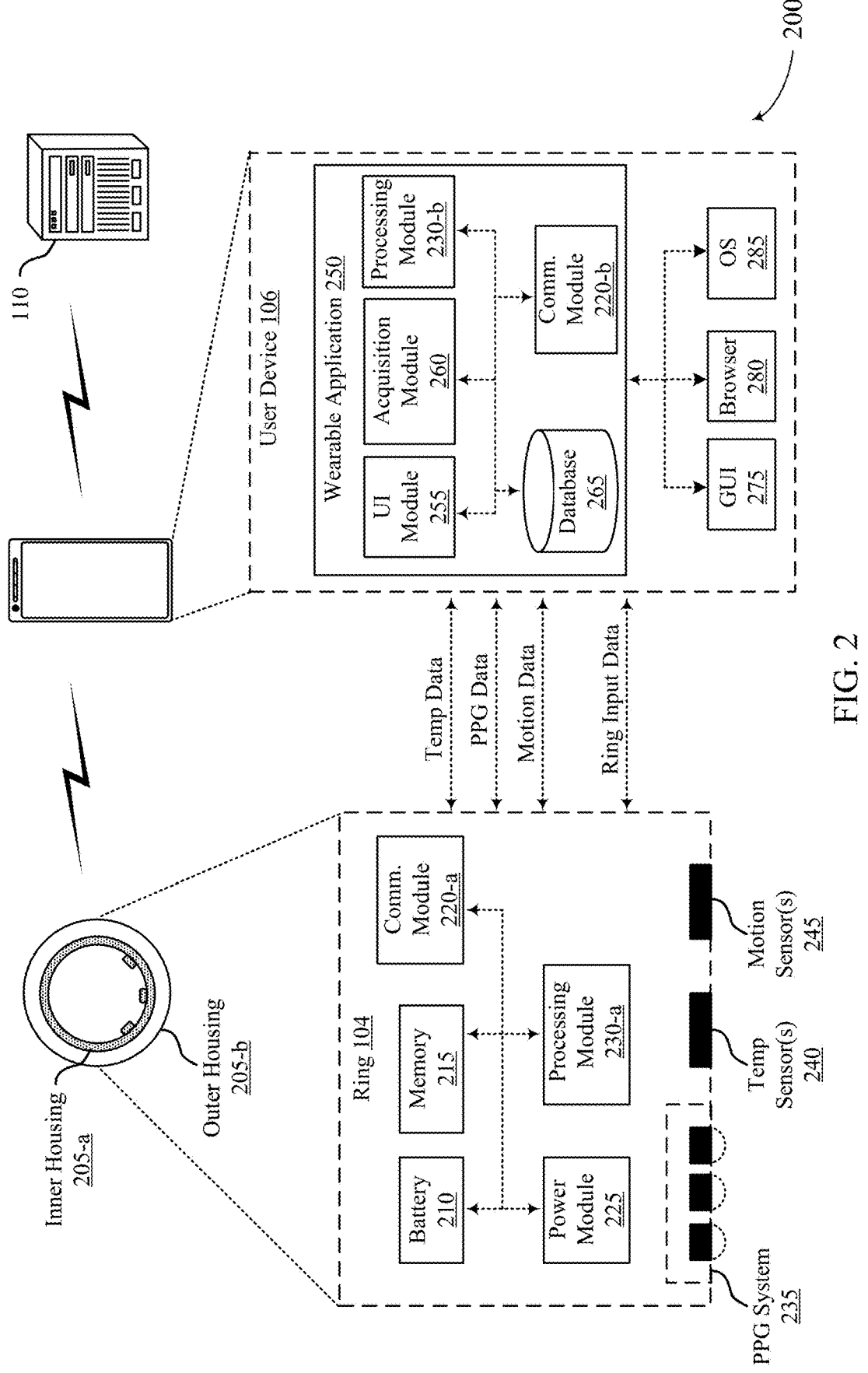
FIG. 2 illustrates an example of a system that supports asymmetric sensor configurations for wearable devices in accordance with aspects of the present disclosure.

FIG. 2 illustrates an example of a system 200 that supports asymmetric sensor configurations for wearable devices in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light-emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be preprocessed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support asymmetric sensor configurations for wearable devices. In particular, a ring 104 may support multiple sensors including a PPG system 235, temp sensors 245, and motion sensors 245. Further, the PPG system 235 may include one or more photodetectors, including a first photodetector, and one or more light-emitting components, such as a first light-emitting component and a second light-emitting component. For example, as shown in FIG. 2, a ring 104 may include an inner housing 205-a configured to contain the first photodetector, the first light-emitting component, and the second light-emitting component.

In some cases, the first light-emitting component may be located at a first radial position within the inner housing 205-a and the second light-emitting component may be located at a second radial position within the inner housing 205-a, such that the first radial position and the second radial position form a segment of the inner circumference with a radial midpoint. Additionally, the first photodetector may be located at a third radial position within the inner housing 205-a that is offset from the radial midpoint, producing an asymmetric sensor configuration. In this regard, the photodetector may be positioned within the inner housing 205-a in an asymmetrical arrangement with respect to the first and second light-emitting components.

In some cases, locating the first photodetector at the third radial position, offset from the radial midpoint, may result in the ring 104 supporting multiple optical paths of different lengths. In other words, the asymmetrical arrangement of the photodetector may enable multiple optical paths with varying optical lengths. That is, a first optical path between the first light-emitting component and the first photodetector may be different in length than a second optical path between the second light-emitting component and the first photodetector. In such cases, the first optical path may support a first penetration depth into a tissue of a user 102 and the second optical path may support a second penetration depth into the tissue of the user 102. Thus, a controller associated with the ring 104, such as a server 110, a processing module 230, an acquisition module 260, or a communication module 220, among other examples, may selectively activate the first light-emitting component, the second light-emitting component, or both, based on a desired optical path.

In some cases, the desired optical path may be based on a signal quality metric (e.g., perfusion index or signal amplitude) associated with each optical path, a power consumption associated with each light-emitting component, a power consumption associated with each photodetector, or any combination thereof. That is, one or more components of the system 200 may measure a signal quality metric associated with each optical path, a power consumption associated with each light-emitting component, a power consumption associated with each photodetector, or any combination thereof. For example, the ring 104 may collect physiological data associated with a blood oxygen saturation of the user 102 via the first optical path between the first light-emitting component and the first photodetector. In some cases, a controller, such as the processing module 230-a, may determine, via the battery module 225, that the ring 104 is low on power. In such cases, the processing module 230-a may configure the ring 104 to collect the physiological data associated with the blood oxygen saturation of the user 102 via the second optical path between the second light-emitting component and the first photodetector (e.g., switch optical paths) based on a lower power consumption associated with the second optical path compared to the first optical path.

In another example, the ring 104 may collect physiological data associated with a blood oxygen saturation of the user 102 via the first optical path between the first light-emitting component and the first photodetector. In some cases, the processing module 230-a, may determine that a signal quality associated with light received by the first photodetector via the first optical path is below a threshold signal quality. In some examples, the processing module 230-a may configure the ring 104 to collect the physiological data associated with the blood oxygen saturation of the user 102 via the second optical path between the second light-emitting component and the first photodetector (e.g., switch optical paths) based on a higher signal quality associated with light received by the first photodetector via the second optical path (e.g., a signal quality above the threshold).

In some other examples, the processing module 230-a may configure the ring 104 to collect the physiological data associated with the blood oxygen saturation of the user 102 via the first optical path between the first light-emitting component and the first photodetector and via the second optical path between the second light-emitting component and the first photodetector (e.g., activate both optical paths). In such cases, the first light-emitting component may transmit light via the first optical path at the same time the second light-emitting component may transmit light via the second optical path, however, the first photodetector may receive the light transmitted by the first light-emitting component via the first optical path and the light transmitted by the second light-emitting component via the second optical path at different times based on the first optical path being different in length than the second optical path.

Figure 3:
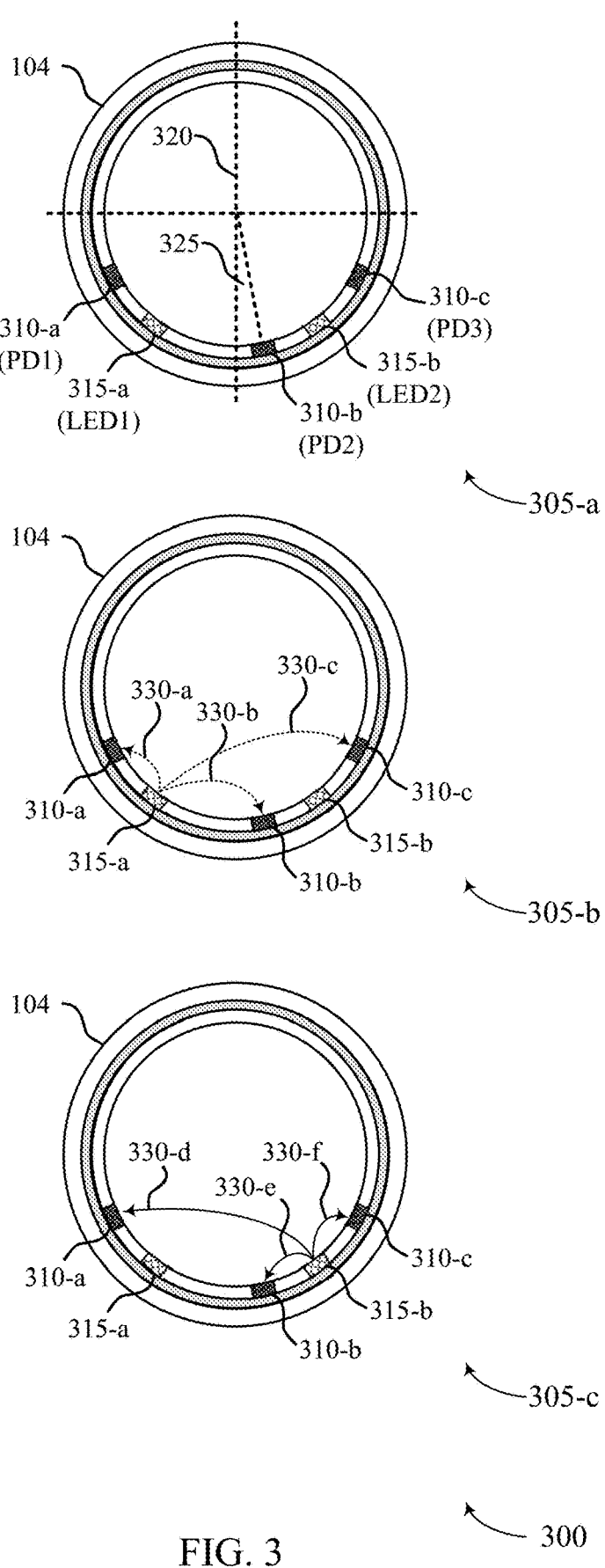
FIG. 3 illustrates an example of a wearable device that supports asymmetric sensor configurations for wearable devices in accordance with aspects of the present disclosure.

FIG. 3 illustrates an example of a wearable device 300 that supports asymmetric sensor configurations for wearable devices in accordance with aspects of the present disclosure. The wearable device 300 may implement, or be implemented by, aspects of the system 100, the system 200, or both.

The wearable device 300 shown in FIG. 3 illustrates an example of a wearable device 104. The wearable device 104 may include one or more photodetectors 310, such as a photodetector 310-a (e.g., PD1), a photodetector 310-b (e.g., PD2), and a photodetector 310-c (e.g., PD3), and one or more light-emitting components (e.g., LEDs 315), such as an LED 315-a (e.g., LED1) and an LED 315-b (e.g., LED2), among other electronic components. In some cases, as depicted in cross sectional view 305-a, a set of photodetectors 310, a set of LEDs 315, or both, may be located at radial positions within an inner circumference of the ring 104.

In some implementations, some of the sensors (e.g., photodetectors 310, LEDs 315) of the ring may be positioned on/within the ring 104 symmetrically with respect to an axis 320 of the ring 104, where at least one sensor (e.g., photodetector 310-b) is positioned asymmetrically with respect to the axis 320 and/or the other sensors.

For example, the first LED 315-a and the second LED 315-b may be located at radial positions within the inner circumferential surface of the ring 104, where the radial positions of the LEDs 315-a, 315-b are symmetrical (e.g., mirrored) with respect to an axis 320 of the ring 104. For example, the axis 320 may intersect a radial midpoint of a first segment between the LEDs 315, such that the LED 315-a and the LED 315-b may be equidistant from each point on the axis 320 (e.g., linearly and angularly). In some cases, the first segment of the inner circumferential surface between the first LED 315-a and the second LED 315-b may be less than 180 degrees.

In another example, the photodetector 310-a and the photodetector 310-c may form a second segment of the inner circumferential surface of the wearable device 104, where the axis 320 may intersect a radial midpoint of the second segment. In this regard, the photodetectors 310-a, 310-c may be equidistant from each point on the axis 320 (e.g., linearly and angularly). In some cases, as depictured in the cross sectional view 305-a, the midpoint of the first segment associated with the set of LEDs 315-a, 315-b may be the same as the midpoint of the second segment associated with the set of photodetectors 310-a, 310-c.

Comparatively, in some cases, one or more sensors, such as a photodetector 310, may be located asymmetrically within an inner circumference of the wearable device 104. That is, a photodetector 310, such as the photodetector 310-b, may be located at a radial position that is offset from the axis 320 (e.g., the photodetector 310-b may not intersect the midpoint of the first section, the second section, or both).

For example, the photodetector 310-*b* may be located at a radial offset from the axis 320 by an angle 325. In this regard, the photodetector 310-*b* may be positioned within the wearable device 104 asymmetrically with respect to the axis 320, the other sensors, or both.

The radial position of the photodetector 310-*b* may enable the wearable device 104 to support multiple optical paths 330 of different lengths. For example, as depicted in cross sectional view 305-*b*, light emitted from the LED 315-*a* may travel along an optical path 330-*a* to the photodetector 310-*a*, along an optical path 330-*b* to the photodetector 310-*b*, and along an optical path 330-*c* to the photodetector 310-*c*. In other words, the photodetector 310-*a* may receive light from the LED 315-*a* along the optical path 330-*a*, the photodetector 310-*b* may receive light from the LED 315-*a* along the optical path 330-*b*, and the photodetector 310-*c* may receive light from the LED 315-*a* along the optical path 330-*c*. In some cases, two or more of the optical path 330-*a*, the optical path 330-*b*, and the optical path 330-*c* may be different in length (e.g., radial distances or offsets between the LED 315-*a* and respective photodetectors 310 may be different). In some cases, each optical path 330 may be associated with a penetration depth into a tissue of a user 102. That is, the optical path 330-*a* may be associated with a first penetration depth, the optical path 330-*b* may be associated with a second penetration depth, and the optical path 330-*c* may be associated with a third penetration depth. In some cases, two or more of the first penetration depth, the second penetration depth, and the third penetration depth may be different (e.g., based on the offset of the photodetector 310-*b*).

In another example, as depicted in cross sectional view 305-*c*, light emitted from the LED 315-*b* may travel along an optical path 330-*d* to the photodetector 310-*a*, along an optical path 330-*e* to the photodetector 310-*b*, and along an optical path 330-*f* to the photodetector 310-*c*. In other words, the photodetector 310-*a* may receive light from the LED 315-*b* along the optical path 330-*a*, the photodetector 310-*b* may receive light from the LED 315-*b* along the optical path 330-*b*, and the photodetector 310-*c* may receive light from the LED 315-*b* along the optical path 330-*c*. In some cases, two or more of the optical path 330-*d*, the optical path 330-*e*, and the optical path 330-*f* may be different in length (e.g., radial distances or offsets between the LED 315-*b* and respective photodetectors 310 may be different). In some cases, each optical path 330 may be associated with a penetration depth into a tissue of a user 102. That is, the optical path 330-*d* may be associated with a first penetration depth, the optical path 330-*e* may be associated with a second penetration depth, and the optical path 330-*f* may be associated with a third penetration depth. In some cases, two or more of the first penetration depth, the second penetration depth, and the third penetration depth may be different (e.g., based on the offset of the photodetector 310-*b*).

Additionally, the light-emitting components described herein (e.g., LEDs 315-*a*, 315-*b*) may be configured to emit light in multiple different wavelength ranges. In some implementations, each LED 315 may include multiple LEDs (e.g., chips) that are configured to emit light (e.g., signals) within a respective wavelength range. For example, each LED 315, such as the LED 315-*a* and the LED 315-*b*, may include a LED chip configured to emit light within a first wavelength range (e.g., red light), a second LED chip configured to emit light within a second wavelength range (e.g., green light), and a third LED chip configured to emit light within a third wavelength range (e.g., infrared (IR) light). In this regard, the LEDs 315-*a*, 315-*b* may be referred to as "triple-LEDs" that are each configured to emit light in three separate wavelength ranges.

As such, light emitted from each LED 315 (e.g., from each light-emitting chip within each LED 315) may travel along each of the optical paths 330. For example, the LED 315-*a* may emit red light from the first light-emitting chip along each optical path 330 (e.g., the optical path 330-*a*, the optical path 330-*b*, and the optical path 330-*c*), emit green light from the second light-emitting chip along each optical path 330, and emit IR light from the third light-emitting chip along each optical path 330. Similarly, the LED 315-*b* may emit red light from the first light-emitting chip along each optical path 330 (e.g., the optical path 330-*d*, the optical path 330-*e*, and the optical path 330-*f*), emit green light from the second light-emitting chip along each optical path 330, and emit IR light from the third light-emitting chip along each optical path 330.

In this regard, the wearable 104 depicted in FIG. 3, may support eighteen measurement (e.g., signal) paths (e.g., channels) for collecting physiological data. That is, the wearable device 104 may include two LEDs 315 (e.g., the LED 315-*a* and the LED 315-*b*), where each LED 315 may include three light-emitting chips capable of emitting light within a respective wavelength range along three different optical paths 330 resulting in eighteen unique measurement paths $$\left( \text{e.g., } 2\,LEDs\,315 \times 3\frac{\text{light emitting diodes}}{LED\,315} \times 3\frac{\text{optical paths}}{LED\,315} \right).$$

In this regard, each of the optical paths 330-*a* through 330-*f* illustrated in the cross-sectional views 305-*b* and 305-*c* may each include three measurement paths (e.g., each optical path 330 includes a red measurement path, a green measurement path, and an IR measurement path in the case of a triple-LED 315). In some cases, each measurement path (e.g., unique measurement path) may be associated with a set of characteristics (e.g., unique characteristics). That is, the system 200 may collect physiological data (e.g., PPG signals) via each measurement path (e.g., in a unique way) based on a wavelength range, a sensor placement (e.g., LED 315 and photodetector 310 location), and anatomy of a finger associated with the user 102. In some cases, the system 200 may correlate physiological data collected via multiple measurement paths (e.g., the eighteen measurement paths) to support noise reduction (e.g., filter noise from the measurements).

For example, the system 200 may collect first physiological data associated with light emitted from the LED 315-*a* to the photodetector 310-*a* via the optical path 330-*a* using the first light-emitting chip, second physiological data associated with light emitted from the LED 315-*a* to the photodetector 310-*a* via the optical path 330-*a* using the second light-emitting chip, and third physiological data associated with light emitted from the LED 315-*a* to the photodetector 310-*a* via the optical path 330-*a* using the third light-emitting chip. The system 200 may collect additional physiological data using each light-emitting chip on the LED 315-*a* along each additional optical path 330 from the LED 315-*a* (e.g., the optical path 330-*b* and the optical path 330-*c*). Additionally, or alternatively, the system 200 may collect additional physiological data using each light-emitting chip on the LED 315-*b* along each optical path 330 (e.g., the optical path 330-*d*, the optical path 330-*e*, and the optical path 330-*f*). Though described in the context of physiological data collection associated with eighteen measurement paths, it is understood that the system 200 may collect physiological data using any quantity or combination of the eighteen measurement paths.

While much of the present disclosure describes light-emitting components (e.g., LEDs 315) as being configured to emit red, green, and IR light, this is not to be regarded as a limitation of the present disclosure, unless noted otherwise herein. In this regard, light-emitting components (e.g., LEDs 315) described herein may be configured to emit light in any number of wavelength ranges (e.g., different colors). For example, light-emitting components may be configured to emit yellow light, blue light, and the like. Light of different wavelength ranges (e.g., different colors of light) may exhibit differing penetration depths, and may therefore be used to perform different types of physiological measurements.

The concept of light-emitting components including multiple LEDs or LED chips (e.g., triple-LEDs) will be further shown and described with reference to FIG. 5.

In some implementations, parameters of the optical paths 330 (e.g., optical path length, penetration depth) may be selectively adjusted by modifying one or more components of the LEDs 315 and/or the photodetectors 310. For example, the penetration depth and length of the respective optical paths 330 may be modified with light angular filtering at the photodetectors 310, or by directing light emission from the LEDs 315. That is, the relative angles at which light is emitted by the LEDs 315 and received by the photodetectors 310 may be modified (e.g., via lenses or other optical components) in order to selectively adjust the penetration depth and/or path length of the optical paths 330.

In some cases, a system 200 associated with the wearable 104 may collect physiological data associated with the user 102 based on light received by the photodetectors 310 from the LEDs 315 along the optical paths 330. For example, a controller communicatively coupled to one or more of the LEDs 315, one or more of the photodetectors 310, or any combination thereof, may collect physiological data associated with the user 102 based on light received by the photodetector 310-*b* and light emitted from the LED 315-*a*, the LED 315-*b*, or both (e.g., along the optical path 330-*b*, the optical path 330-*e*, or both).

In some cases, the controller may selectively activate one or more of the LEDs 315 (e.g., light-emitting chips within the LEDs 315) based on a respective signal quality metric associated with light received by one or more of the photodetectors 310. For example, a first signal quality metric may be associated with light received by the photodetector 310-*b* from the LED 315-*a* via the optical path 330-*b* and a second signal quality metric may be associated with light received by the photodetector 310-*b* from the LED 315-*b* via the optical path 330-*e*. In some cases, the controller may selectively activate one or more of the LEDs 315 based on a respective signal quality metric associated with light received by one or more of the photodetectors 310 dropping below a threshold (e.g., failing to exceed the threshold). For example, the system 200 may collect physiological data based on light received from the photodetector 310-*b* from the LED 315-*a* via the optical path 330-*b*, where the light received via the optical path 330-*b* is associated with the first signal quality metric. In some cases, the first signal quality metric may drop below the threshold and the controller activates the LED 315-*a* such that the system 200 may collect physiological data based on light received from the photodetector 310-*b* from the LED 315-*b* via the optical path 330-*e*.

In some cases, the controller may deactivate the LED 315-*a* based on activating the LED 315-*b*. In some other cases, the controller may activate the LED 315-*a* and the LED 315-*b* such that the photodetector receives light from the LED 315-*a* via the optical path and receives light from the LED 315-*b* via the optical path 330-*e*. In such cases, the LED 315-*a* and the LED 315-*b* may emit respective light at the same time (e.g., simultaneously), however, due to a difference in length between the optical path 330-*b* and the optical path 330-*e*, the photodetector 310-*b* may receive light from the LED 315-*a* and light from the LED 315-*b* at different times. In other words, due to the varying optical path lengths of the optical path 330-*b* and the optical path 330-*e*, the first LED 315-*a* and the second LED 315-*b* may be activated at the same time (e.g., simultaneously), where the varying optical path lengths cause light emitted by the respective LEDs 315 to arrive at the photodetector 310-*b* at different times. In such cases, due to the different arrival times of the light, the photodetector 310-*b* may be able to differentiate between the light emitted by the respective LEDs 315, even though the LEDs 315 were activated at the same time.

Additionally, or alternatively, the controller may selectively activate one or more of the LEDs 315 (e.g., light-emitting diodes) or photodetectors 310 based on a respective power consumption associated with light received by one or more of the photodetectors 310. For example, a first power consumption may be associated with the LED 315-*a* and a second power consumption may be associated with the LED 315-*b*. In some cases, the first power consumption may be less than the second power consumption, such that the controller may activate the LED 315-*a* based on the wearable device 104 operating in a low power mode. In some other cases, the controller may activate the LED 315-*b* or both LEDs 315 based on the wearable device 104 operating in a high power mode. In some cases, the system 200 may selectively activate one or more of the LEDs 315 (e.g., light-emitting chips) based on a rotation of the wearable device 104. Similarly, a third power consumption may be associated with the photodetector 310-*a*, a fourth power consumption may be associated with the photodetector 310-*b*, and a fifth power consumption may be associated with the photodetector 310-*c*, such that the controller may selectively activate one or more of the photodetectors 310 based on a power mode associated with the wearable device 104.

While FIG. 3 is shown and described as a wearable device 104 with photodetectors 310 and LEDs 315, this is not to be regarded as a limitation of the present disclosure, unless noted otherwise herein. In this regard, aspects of the present disclosure may be implemented in the context of any quantity or type of sensors (e.g., electrical components, including but not limited to LEDs 315 and photodetectors 310).

It has been found that placing an LED 315 and a photodetector 310 too close together, or too far apart, may result in poor quality physiological measurements. In this regard, there are "optimal" distances/ranges between LEDs 315 and photodetectors 310 that may result in accurate physiological data measurement. An optimal LED-PD range may be defined by a range of radial offsets (and/or range of linear distances) between an LED 315 and a photodetector 310 on the inner circumferential surface of the wearable device 104. For example, it has been found that a linear offset between an LED 315 and a photodetector 310 of three and five millimeters results in the highest quality measurements (e.g., optimal LED-PD range of 3-5 mm).

In some aspects, the asymmetrical sensor configuration may result in larger quantities/proportions of LED-PD distances that are inside the ideal/optimal range of sensor LED-PD distances for most ring sizes, including the most common ring size of US10. In other words, the asymmetrical sensor configuration enables LEDs 315 to be radially offset from photodetectors 310 (and vice versa) within the optimal LED-PD ranges for more sizes of rings. As such, the asymmetrical design may provide more candidate optical paths 330 for a larger proportion of people when the distribution of ring sizes to users is considered.

Figure 4:
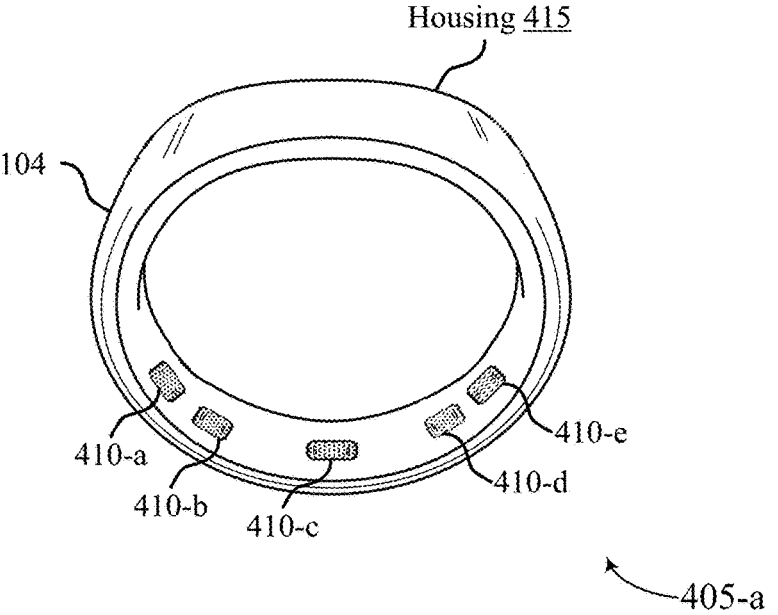
FIG. 4 illustrates an example of a wearable device that supports asymmetric sensor configurations for wearable devices in accordance with aspects of the present disclosure.
Figure 4:
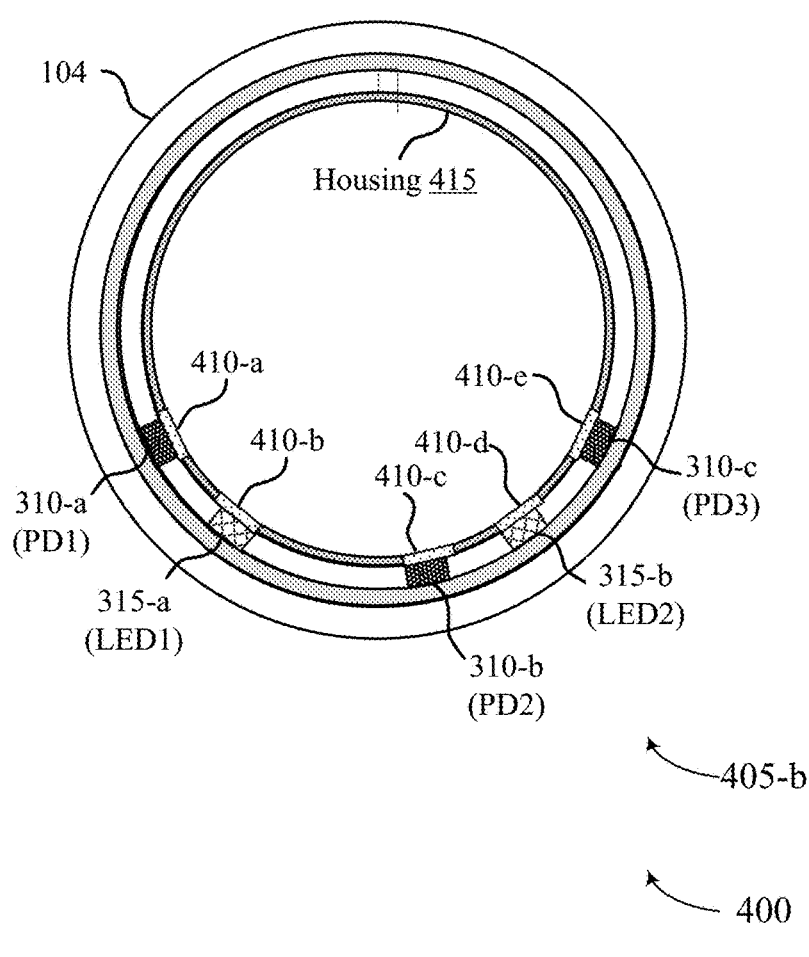

In some implementations, the asymmetrical sensor configuration of the wearable device 104 (e.g., wearable ring device 104) illustrated in FIG. 4 may provide improved robustness against rotation of the wearable device 104 when being worn by the user. That is, as compared to wearable devices 104 with symmetrical sensor configurations, the asymmetrical sensor configuration may enable improved physiological data measurement in cases where the wearable device 104 is inadvertently rotated while being worn by the user. The improved robustness against device rotation may result from the combination of multiple alternative optical paths 330, and adaptive selection of the optical path 330/ measurement path that exhibits the highest quality and/or lowest power consumption. As such, the asymmetrical sensor configuration, along with the hardware configuration that enables multiple candidate optical paths 330 around the circumference of the wearable device 104, may result in improved robustness to device rotation.

For example, in the context of SpO2 measurement with a wearable ring device 104, the wearable ring device 104 may include four separate optical paths 330 (e.g., optical paths 330-a, 330-b, 330-e, 330-f) that exhibit optimal distances between the respective photodetectors 310 and LEDs 315 resulting in penetration depths that enable high quality SpO2 measurements. As such, the asymmetrical sensor configuration provides for more optical paths 330 that may be used to perform SpO2 measurements, thereby increasing the likelihood that at least one of the optical paths 330 may be used for SpO2 measurements, regardless as to how the wearable ring device 104 is rotated on the user's finger. Comparatively, wearable ring devices 104 that include symmetrical sensor configurations may include two (or only one) optical path that may be used for accurate SpO2 measurements, thereby making wearable ring devices 104 with symmetrical sensor configurations more sensitive and susceptible to inadvertent rotation. Similar benefits associated with robustness to rotation may be provided in the context of other physiological measurements in addition to SpO2 measurements, such as heart rate measurements.

FIG. 4 illustrates an example of a wearable device 400 that supports asymmetric sensor configurations for wearable devices in accordance with aspects of the present disclosure. The wearable device 400 may implement, or be implemented by, aspects of the system 100, the system 200, or both.

The wearable device 400 shown in FIG. 4 illustrates an example of a wearable device 104. As depicted in a perspective view 405-a, the wearable device 104 may include one or more photodetectors 310, such as the photodetector 310-a (e.g., PD1), the photodetector 310-b (e.g., PD2), and the photodetector 310-c (e.g., PD3), and one or more light-emitting components (e.g., LEDs 315), such as the LED 315-a (e.g., LED1) and the LED 315-b (e.g., LED2), among other electronic components, described with reference to FIG. 3.

Additionally, as depicted in a cross sectional view 405-b, the photodetectors 310 and the LEDs 315 may be offset from an inner surface of the wearable device 104, such that a housing 415 (e.g., ring housing 415) exists between the photodetectors 310 and the LEDs 315 and the inner surface of the wearable device 104. In other words, the LEDs 315 and the photodetectors 310 may be positioned within and/or behind an inner circumferential surface of the housing 415. In some implementations, the housing 415 may include a metal housing. In other cases, the housing 415 may be made up of different materials, such as plastic, ceramic, epoxy, etc. In some cases, the housing 415 may be at least partially transparent or translucent. In other cases, the housing 415 may be at least partially opaque such that light emitted from the LEDs 315 is not able to penetrate or pass through the housing 415.

As such, the wearable device 104 may include one or more apertures 410 (e.g., metallic inlet optical apertures 410) in the housing 415, such as an aperture 410-a, an aperture 410-b, an aperture 410-c, an aperture 410-d, and an aperture 410-e. In such cases, each aperture 410 may be associated with a photodetector 310 or an LED 315 such that respective photodetectors 310 and LEDs 315 may emit or receive light through a respective aperture 410. For example, the aperture 410-a may be associated with the photodetector 310-a, the aperture 410-b may be associated with the LED 315-a, the aperture 410-c may be associated with the photodetector 310-b, the aperture 410-d may be associated with the LED 315-b, and the aperture 410-a may be associated with the photodetector 310-c.

In some aspects, the apertures 410 may include holes in the housing 415. In additional or alternative implementations, the apertures 410 may include lenses, separate opaque pieces with openings, or other optical components. For example, in some cases, the apertures 410 may include lenses or other optical components that may be used to selectively modify an angle with which light is transmitted from the LEDs 315 and/or received by the photodetectors 310. As described previously herein, the penetration depth and/or path length of the optical paths 330 may be selectively modified by adjusting the angles with which light is emitted by the LEDs 315 and/or received by the photodetectors 310.

In some cases, one or more of the apertures 410 may be offset from the corresponding photodetector 310 or LED 315. That is, a center point of an aperture 410 may not be aligned with (e.g., may be offset relative to) a center point of an associated photodetector 310 or LED 315. For example, the aperture 410-c may be offset from the photodetector 310-b, such that the aperture 410-c is offset towards the LED 315-a. In another example, the aperture 410-b and the aperture 410-d may be offset from the LED 315-a and the LED 315-b, respectively, such that the aperture 410-b and the aperture 410-d are offset away from the photodetector 310-b. In some aspects, the relative radial offsets of the apertures 410 with respect to the LEDs 315/photodetectors 310 may be based on (e.g., may be proportional to) the relative radial offset of the photodetector 310-b with respect to the axis 320 of the ring 104, as shown and described in FIG. 3.

In some other cases, one or more of the apertures 410 may not be offset from an associated (e.g., respective) photodetector 310 or LED 315. That is, a center point of an aperture 410 may be aligned with (e.g., may not be offset relative to)

a center point of an associated photodetector 310 or LED 315, described with reference to FIG. 5. For example, the aperture 410-a and the aperture 410-e may not be offset from the photodetector 310-a and the photodetector 310-c. In other words, center points of the aperture 410-a and the aperture 410-e may be aligned with center points of photodetector 310-a and the photodetector 310-c, respectively.

In some cases, one or more of the apertures 410 may be the same in length and/or width. Additionally, or alternatively, one or more of the apertures 410 may be a different in length and/or width. In some cases, a size of the apertures 410 may be independent of a circumference of the housing 415.

Figure 5:
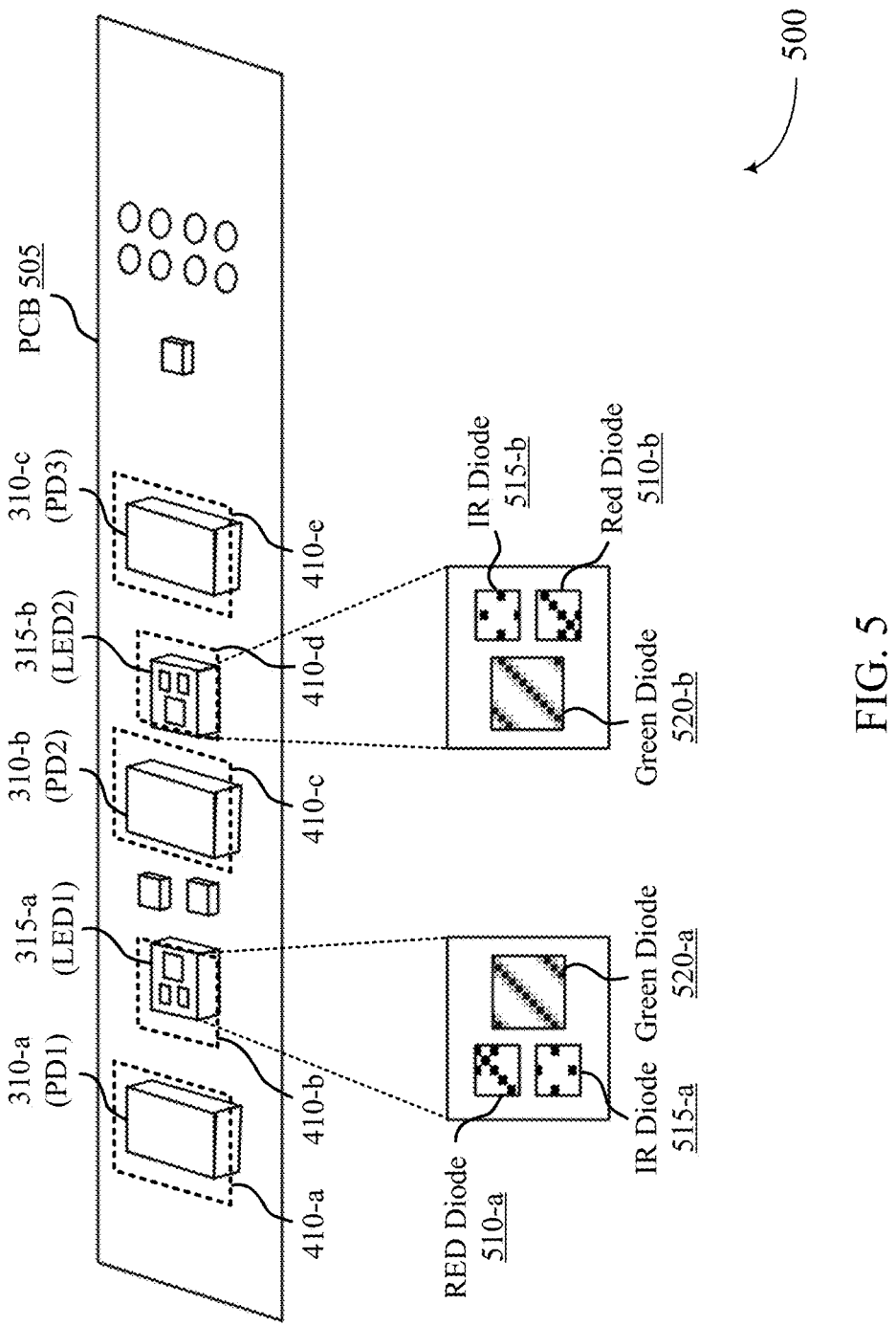
FIG. 5 illustrates an example of an electronic layout and components that support asymmetric sensor configurations for wearable devices in accordance with aspects of the present disclosure.

FIG. 5 illustrates an example of an electronic component 500 that supports asymmetric sensor configurations for wearable devices in accordance with aspects of the present disclosure. The electronic component 500 may implement, or be implemented by, aspects of the system 100, the system 200, the wearable device 300, the wearable device 400, or any combination thereof.

The electronic component 500 shown in FIG. 5 illustrates an example of a PCB 505. In some cases, the PCB 505 may be included in a wearable device 104. For example, the PCB 505 may be at least partially positioned or contained within the housing 415 illustrated in FIG. 4. Additionally, the PCB 505 may include multiple sensors, such as one or more photodetectors 310, including the photodetector 310-a, the photodetector 310-b, and the photodetector 310-c, and one or more LEDs 315, such as the LED 315-a and the LED 315-b, described with reference to FIG. 3.

In some cases, each LED 315 may include one or more light-emitting chips or components, such as a red diode (e.g., LED) 510, an IR diode 515, and a green diode 520. For example, the LED 315-a may include a red diode 510-a, an IR diode 515-a, and a green diode 520-a. Similarly, the LED 315-b may include a red diode 510-b, an IR diode 515-b, and a green diode 520-b. Additionally, each diode may be configured to (e.g., be capable of) emitting light within a respective wavelength range. For example, a red diode 510 may emit light within a first wavelength range (e.g., red light), an IR diode 515 may emit light within a second wavelength range (e.g., IR light), and a green diode 520 may emit light within a third wavelength range (e.g., green light). In some cases, the first wavelength range, the second wavelength range, and the third wavelength range may be unique (e.g., different).

Though described in the context of red diodes 510, IR diodes 515, and green diodes 520, it is understood that diodes on an LED 315 may be associated with any color of light within a spectrum. That is, a diode may be configured to emit light within a wavelength range not limited to the first wavelength range, the second wavelength range, or the third wavelength range. For example, as described previously herein, light-emitting components of the present disclosure (e.g., LEDs 315) may include additional diodes configured to emit light in any wavelength range of color, such as yellow light, blue light, etc.

In some cases, the location of each diode on an LED 315 (e.g., arrangement of diodes on the LED 315) may be based on the location of one or more sensors. For example, green diodes 520 may be located on a side of an LED 315 closest to a photodetector 310 (e.g., closest to a central photodetector 310 in relation to red diodes 510 and IR diodes 515), such as the photodetector 310-b (e.g., a photodetector 310 located at an asymmetric position). For example, the green diode 520-a may be located on a side of the LED 315-a closest to the photodetector 310-b (e.g., the right side) and the green diode 520-b may be located on a side of the LED 315-b closest to the photodetector 310-b (e.g., the left side). In such cases, a signal quality metric associated with emission of light from the green diode 520-a on the LED 315-a to the photodetector 310-b may be higher than a signal quality metric associated with emission of light from the green diode 520-a on the LED 315-a to the photodetector 310-a (e.g., due to a location of the green diode 520-a closer to the photodetector 310-b). Similarly, a signal quality metric associated with emission of light from the green diode 520-b on the LED 315-b to the photodetector 310-b may be higher than a signal quality metric associated with emission of light from the green diode 520-b on the LED 315-b to the photodetector 310-c (e.g., due to a location of the green diode 520-b closer to the photodetector 310-b).

In another example, red diodes 510 and IR diodes 515 may be located on a side of an LED 315 furthest from the photodetector 310 (e.g., furthest from a central photodetector 310 in relation to green diodes 520), such as the photodetector 310-b. For example, the red diode 510-a and the IR diode 515-a may be located on a side of the LED 315-a furthest from the photodetector 310-b (e.g., the left side) and the red diode 510-b and the IR diode 515-b may be located on a side of the LED 315-b furthest from photodetector 310-b (e.g., the right side). In such cases, a signal quality metric associated with emission of light from the red diode 510-a or the IR diode 515-a on the LED 315-a to the photodetector 310-a may be higher than a signal quality metric associated with emission of light from the red diode 510-a or the IR diode 515-a, respectively, on the LED 315-a to the photodetector 310-b (e.g., due to a location of the red diode 510-a or the IR diode 515-a closer to the photodetector 310-a or due to biological characteristics of the user, such as tissue structure, associated with an optical path between the red diode 510-a or the IR diode 515-a to the photodetector 310-a). Similarly, a signal quality metric associated with emission of light from the red diode 510-b or the IR diode 515-b on the LED 315-b to the photodetector 310-c may be higher than a signal quality metric associated with emission of light from the red diode 510-a or the IR diode 515-a, respectively, on the LED 315-b to the photodetector 310-b (e.g., due to a location of the red diode 510-b or the IR diode 515-b closer to the photodetector 310-c or due to biological characteristics of the user, such as tissue structure, associated with an optical path between the red diode 510-b or the IR diode 515-b to the photodetector 310-c).

Additionally, each sensor (e.g., each photodetector 310 and each LED 315) may be associated with an aperture 410, such as the aperture 410-a, the aperture 410-b, the aperture 410-c, the aperture 410-d, and the aperture 410-e, where each aperture 410 is offset from a respective sensor, described with reference to FIG. 4.

In some cases, one or more of the apertures 410 may be offset from an associated (e.g., respective) photodetector 310 or LED 315. That is, on the PCB 505, a center point of an aperture 410 may not be aligned along a first direction with (e.g., may be offset from) a center point of an associated photodetector 310 or LED 315. For example, the aperture 410-c may be offset from the photodetector 310-b, such that the aperture 410-c is offset towards the LED 315-a. In another example, the aperture 410-b and the aperture 410-d may be offset from the LED 315-a and the LED 315-b, respectively, such that the aperture 410-b and the aperture 410-d are offset away from the photodetector 310-b.

In some other cases, one or more of the apertures 410 may not be offset from an associated (e.g., respective) photodetector 310 or LED 315. That is, on the PCB 505, a center point of an aperture 410 may be aligned along the first direction with (e.g., not be offset from) a center point of an associated photodetector 310 or LED 315, described with reference to FIG. 5. For example, the aperture 410-*a* and the aperture 410-*e* may not be offset from the photodetector 310-*a* and the photodetector 310-*c*.

While FIG. 5 is shown and described as a PCB 505 with photodetectors 310, LEDs 315, and apertures 410, this is not to be regarded as a limitation of the present disclosure, unless noted otherwise herein. In this regard, aspects of the present disclosure may be implemented in the context of any quantity or type of sensors (e.g., electrical components, including but not limited to LEDs 315 and photodetectors 310).

Figure 6:
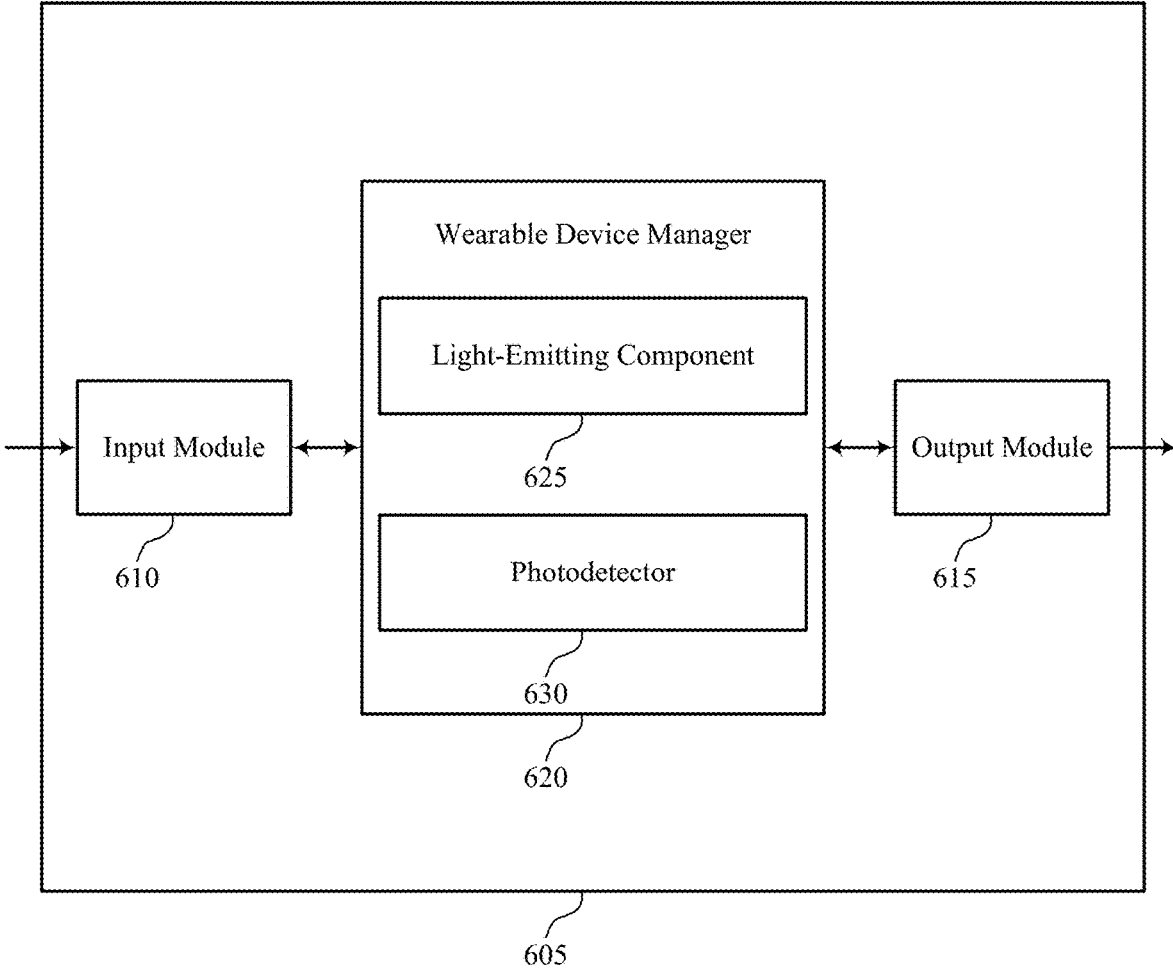
FIG. 6 shows a block diagram of an apparatus that supports asymmetric sensor configurations for wearable devices in accordance with aspects of the present disclosure.

FIG. 6 shows a block diagram 600 of a device 605 that supports asymmetric sensor configurations for wearable devices in accordance with aspects of the present disclosure. The device 605 may include an input module 610, an output module 615, and a wearable device manager 620. The device 605 may also include a processor. Each of these components may be in communication with one another (e.g., via one or more buses).

For example, the wearable device manager 620 may include a light-emitting component 625 a photodetector 630, or any combination thereof. In some examples, the wearable device manager 620, or various components thereof, may be configured to perform various operations (e.g., receiving, monitoring, transmitting) using or otherwise in cooperation with the input module 610, the output module 615, or both. For example, the wearable device manager 620 may receive information from the input module 610, send information to the output module 615, or be integrated in combination with the input module 610, the output module 615, or both to receive information, transmit information, or perform various other operations as described herein.

The light-emitting component 625 may be configured as or otherwise support a means for a first light-emitting component configured to emit light within at least a first wavelength range, the first light-emitting component positioned within an inner circumferential surface of the wearable ring device at a first radial position. The light-emitting component 625 may be configured as or otherwise support a means for a second light-emitting component configured to emit light within at least the first wavelength range, the second light-emitting component positioned within the inner circumferential surface of the wearable ring device at a second radial position, wherein the first radial position and the second radial position define a segment of the inner circumferential surface between the first radial position and the second radial position. The photodetector 630 may be configured as or otherwise support a means for a photodetector configured to receive light emitted by the first light-emitting component and the second light-emitting component, the photodetector positioned at a third radial position within the segment of the inner circumferential surface between the first radial position and the second radial position, wherein the third radial position is offset from a radial midpoint of the segment such that a first radial distance between the photodetector and the first light-emitting component is greater than a second radial distance between the photodetector and the second light-emitting component.

Figure 7:
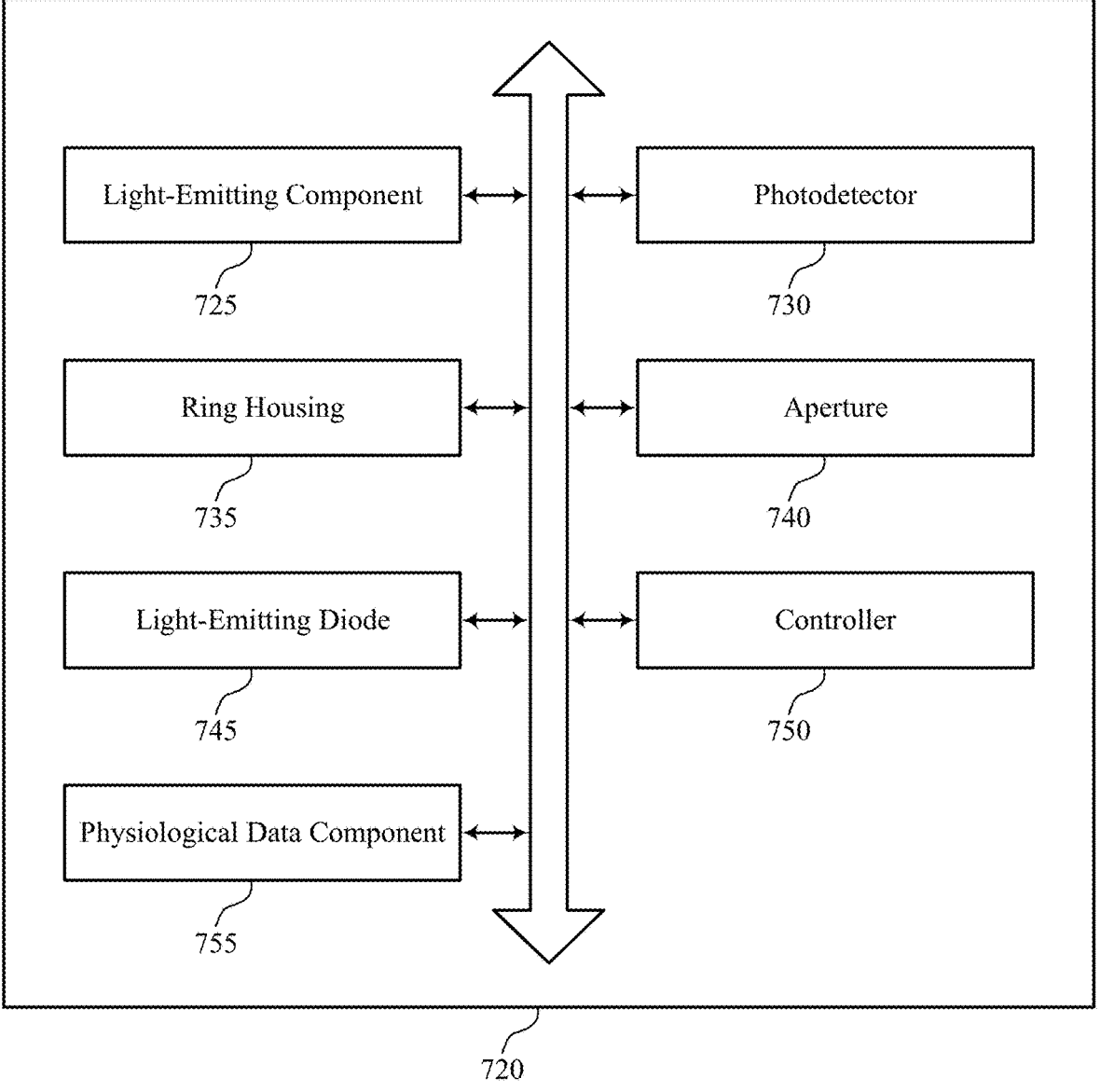
FIG. 7 shows a block diagram of a wearable device manager that supports asymmetric sensor configurations for wearable devices in accordance with aspects of the present disclosure.

FIG. 7 shows a block diagram 700 of a wearable device manager 720 that supports asymmetric sensor configurations for wearable devices in accordance with aspects of the present disclosure. The wearable device manager 720 may be an example of aspects of a wearable device manager or a wearable device manager 620, or both, as described herein. The wearable device manager 720, or various components thereof, may be an example of means for performing various aspects of asymmetric sensors for wearable devices as described herein. For example, the wearable device manager 720 may include a light-emitting component 725, a photodetector 730, a housing 735, an aperture 740, a light-emitting diode 745, a controller 750, a physiological data component 755, or any combination thereof. Each of these components may communicate, directly or indirectly, with one another (e.g., via one or more buses).

The light-emitting component 725 may be configured as or otherwise support a means for a first light-emitting component configured to emit light within at least a first wavelength range, the first light-emitting component positioned within an inner circumferential surface of the wearable device at a first radial position. In some examples, the light-emitting component 725 may be configured as or otherwise support a means for a second light-emitting component configured to emit light within at least the first wavelength range, the second light-emitting component positioned within the inner circumferential surface of the wearable device at a second radial position, wherein the first radial position and the second radial position define a segment of the inner circumferential surface between the first radial position and the second radial position. The photodetector 730 may be configured as or otherwise support a means for a photodetector configured to receive light emitted by the first light-emitting component and the second light-emitting component, the photodetector positioned at a third radial position within the segment of the inner circumferential surface between the first radial position and the second radial position, wherein the third radial position is offset from a radial midpoint of the segment such that a first radial distance between the photodetector and the first light-emitting component is greater than a second radial distance between the photodetector and the second light-emitting component.

In some examples, the housing 735 may be configured as or otherwise support a means for a housing configured to contain at least portions of the first light-emitting component, the second light-emitting component, and the photodetector. In some examples, the aperture 740 may be configured as or otherwise support a means for a first aperture disposed within the inner circumferential surface of the housing, the first aperture configured to direct light from the first light-emitting component through the housing. In some examples, the aperture 740 may be configured as or otherwise support a means for a second aperture disposed within the inner circumferential surface of the housing, the second aperture configured to direct light from the second light-emitting component through the housing. In some examples, the aperture 740 may be configured as or otherwise support a means for a third aperture disposed within the inner circumferential surface of the housing, the third aperture configured to direct light through the housing to the photodetector.

In some examples, the first aperture is positioned within the housing relative to the first light-emitting component according to a first radial offset. In some examples, the second aperture is positioned within the housing relative to the second light-emitting component according to a second radial offset. In some examples, the first radial offset, the second radial offset, or both, are based at least in part on the third radial position of the photodetector being offset from the radial midpoint of the segment.

In some examples, the first radial offset and the second radial offset comprise radial offsets away from the third radial position of the photodetector.

In some examples, the third aperture is positioned within the housing relative to the photodetector according to a third radial offset based at least in part on the third radial position of the photodetector being offset from the radial midpoint of the segment.

In some examples, the third radial offset comprises a radial offset toward the second radial position of the second light-emitting component.

In some examples, the housing comprises a metal housing.

In some examples, the photodetector is configured to receive light via a first optical path between the first light-emitting component and the photodetector, and via a second optical path between the second light-emitting component and the photodetector. In some examples, the first optical path is associated with a first penetration depth into a tissue of a user and. In some examples, the second optical path is associated with a second penetration depth into the tissue of the user. In some examples, a difference between the first penetration depth and the second penetration depth is based at least in part on the third radial position of the photodetector being offset from the radial midpoint of the segment.

In some examples, a first light-emitting diode configured to emit light within the first wavelength range. In some examples, a second light-emitting diode configured to emit light within a second wavelength range different from the first wavelength range. In some examples, a third light-emitting diode configured to emit light within a third wavelength range different from the first wavelength range and the second wavelength range.

In some examples, each of the first wavelength range, the second wavelength range, and the third wavelength range are associated with one of red light, green light, and infrared light.

In some examples, the segment of the inner circumferential surface between the first radial position and the second radial position is less than 180 degrees.

In some examples, the controller 750 may be configured as or otherwise support a means for a controller communicatively coupled to the first light-emitting component, the second light-emitting component, the photodetector, or any combination thereof, wherein the controller is configured to. In some examples, the controller 750 may be configured as or otherwise support a means for acquire physiological data associated with a user based at least in part on light received by the photodetector, the light emitted by the first light-emitting component, the second light-emitting component, or both.

In some examples, selectively activate the first light-emitting component, the second light-emitting component, or both, based at least in part on a first signal quality metric associated with light received by the photodetector via the first optical path, a second signal quality metric associated with light received by the photodetector via the first optical path, a first power consumption associated with the first light-emitting component, a second power consumption associated with the second light-emitting component, or any combination thereof, wherein acquiring the physiological data is based at least in part on selectively activating the first light-emitting component, the second light-emitting component, or both.

In some examples, selectively activate both the first light-emitting component and the second light-emitting component during a first time interval, wherein acquiring the physiological data is based at least in part on selectively activating the first light-emitting component and the second light-emitting component during the first time interval.

In some examples, first light transmitted by the first light-emitting component during the first time interval and received by the photodetector via the first optical path at a second time interval subsequent to the first time interval. In some examples, second light transmitted by the second light-emitting component during the first time interval and received by the photodetector via the second optical path at a third time interval subsequent to the first time interval and prior to the second time interval, wherein a difference between the second time interval and the third time interval is based at least in part on a difference between a first length of the first optical path and a second length of the second optical path.

In some examples, the physiological data comprises heart rate data and blood oxygen saturation data.

Figure 8:
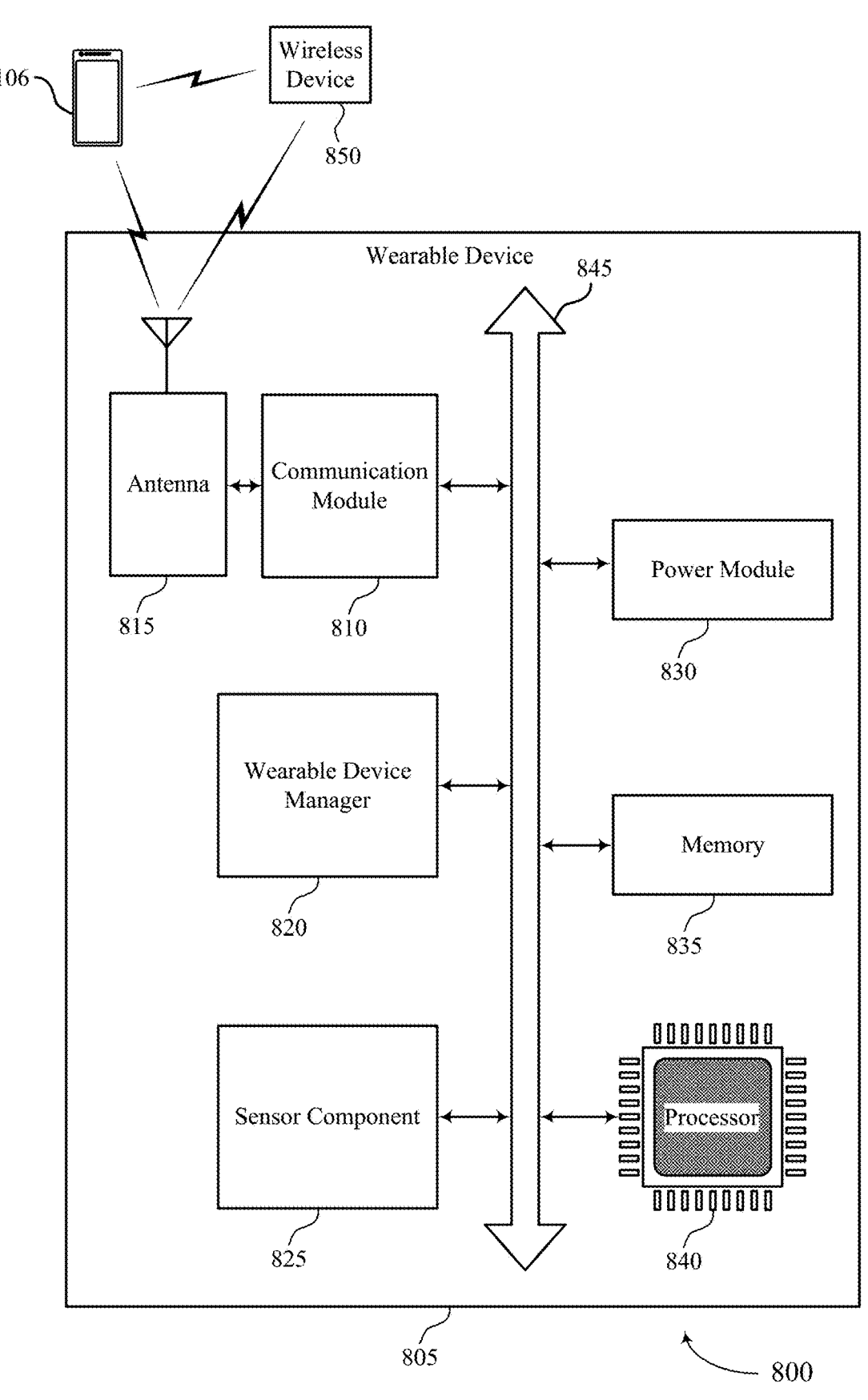
FIG. 8 shows a diagram of a system including a device that supports asymmetric sensor configurations for wearable devices in accordance with aspects of the present disclosure.

FIG. 8 shows a diagram of a system 800 including a device 805 that supports asymmetric sensor configurations for wearable devices in accordance with aspects of the present disclosure. The device 805 may be an example of or include the components of a device 605 as described herein. The device 805 may include an example of a wearable device 104, as described previously herein. The device 805 may include components for bi-directional communications including components for transmitting and receiving communications with a user device 106 and a server 110, such as a wearable device manager 820, a communication module 810, an antenna 815, a sensor component 825, a power module 830, a memory 835, a processor 840, and a wireless device 850. These components may be in electronic communication or otherwise coupled (e.g., operatively, communicatively, functionally, electronically, electrically) via one or more buses (e.g., a bus 845).

For example, the wearable device manager 820 may be configured as or otherwise support a means for a first light-emitting component configured to emit light within at least a first wavelength range, the first light-emitting component positioned within an inner circumferential surface of the wearable device at a first radial position. The wearable device manager 820 may be configured as or otherwise support a means for a second light-emitting component configured to emit light within at least the first wavelength range, the second light-emitting component positioned within the inner circumferential surface of the wearable device at a second radial position, wherein the first radial position and the second radial position define a segment of the inner circumferential surface between the first radial position and the second radial position. The wearable device manager 820 may be configured as or otherwise support a means for a photodetector configuring to receive light emitted by the first light-emitting component and the second light-emitting component, the photodetector positioned at a third radial position within the segment of the inner circumferential surface between the first radial position and the second radial position, wherein the third radial position is offset from a radial midpoint of the segment such that a first radial distance between the photodetector and the first light-emitting component is greater than a second radial distance between the photodetector and the second light-emitting component.

By including or configuring the wearable device manager 820 in accordance with examples as described herein, the device 805 may support asymmetric sensor configurations for wearable devices which may result in increased accuracy of physiological data and reduced power consumption, among other advantages.

It should be noted that the methods described above describe possible implementations, and that the operations and the steps may be rearranged or otherwise modified and that other implementations are possible. Furthermore, aspects from two or more of the methods may be combined.

A method is described. The method may include a first light-emitting component configured to emit light within at least a first wavelength range, the first light-emitting component positioned within an inner circumferential surface of the wearable device at a first radial position, a second light-emitting component configured to emit light within at least the first wavelength range, the second light-emitting component positioned within the inner circumferential surface of the wearable device at a second radial position, wherein the first radial position and the second radial position define a segment of the inner circumferential surface between the first radial position and the second radial position, and a photodetector configured to receive light emitted by the first light-emitting component and the second light-emitting component, the photodetector positioned at a third radial position within the segment of the inner circumferential surface between the first radial position and the second radial position, wherein the third radial position is offset from a radial midpoint of the segment such that a first radial distance between the photodetector and the first light-emitting component is greater than a second radial distance between the photodetector and the second light-emitting component.

An apparatus is described. The apparatus may include a processor, memory coupled with the processor, and instructions stored in the memory. The instructions may be executable by the processor to cause the apparatus to a first light-emit component configured to emit light within at least a first wavelength range, the first light-emitting component positioned within an inner circumferential surface of the wearable device at a first radial position, a second light-emit component configured to emit light within at least the first wavelength range, the second light-emitting component positioned within the inner circumferential surface of the wearable device at a second radial position, wherein the first radial position and the second radial position define a segment of the inner circumferential surface between the first radial position and the second radial position, and a photodetector configure to receive light emitted by the first light-emitting component and the second light-emitting component, the photodetector positioned at a third radial position within the segment of the inner circumferential surface between the first radial position and the second radial position, wherein the third radial position is offset from a radial midpoint of the segment such that a first radial distance between the photodetector and the first light-emitting component is greater than a second radial distance between the photodetector and the second light-emitting component.

Another apparatus is described. The apparatus may include means for a first light-emitting component configured to emit light within at least a first wavelength range, the first light-emitting component positioned within an inner circumferential surface of the wearable device at a first radial position, means for a second light-emitting component configured to emit light within at least the first wavelength range, the second light-emitting component positioned within the inner circumferential surface of the wearable device at a second radial position, wherein the first radial position and the second radial position define a segment of the inner circumferential surface between the first radial position and the second radial position, and means for a photodetector configured to receive light emitted by the first light-emitting component and the second light-emitting component, the photodetector positioned at a third radial position within the segment of the inner circumferential surface between the first radial position and the second radial position, wherein the third radial position is offset from a radial midpoint of the segment such that a first radial distance between the photodetector and the first light-emitting component is greater than a second radial distance between the photodetector and the second light-emitting component.

A non-transitory computer-readable medium storing code is described. The code may include instructions executable by a processor to a first light-emit component configured to emit light within at least a first wavelength range, the first light-emitting component positioned within an inner circumferential surface of the wearable device at a first radial position, a second light-emit component configured to emit light within at least the first wavelength range, the second light-emitting component positioned within the inner circumferential surface of the wearable device at a second radial position, wherein the first radial position and the second radial position define a segment of the inner circumferential surface between the first radial position and the second radial position, and a photodetector configure to receive light emitted by the first light-emitting component and the second light-emitting component, the photodetector positioned at a third radial position within the segment of the inner circumferential surface between the first radial position and the second radial position, wherein the third radial position is offset from a radial midpoint of the segment such that a first radial distance between the photodetector and the first light-emitting component is greater than a second radial distance between the photodetector and the second light-emitting component.

In some examples of the method, apparatuses, and non-transitory computer-readable medium described herein, a housing configured to contain at least portions of the first light-emitting component, the second light-emitting component, and the photodetector, a first aperture disposed within the inner circumferential surface of the housing, the first aperture configured to direct light from the first light-emitting component through the housing, a second aperture disposed within the inner circumferential surface of the housing, the second aperture configured to direct light from the second light-emitting component through the housing, and a third aperture disposed within the inner circumferential surface of the housing, the third aperture configured to direct light through the housing to the photodetector.

In some examples of the method, apparatuses, and non-transitory computer-readable medium described herein, the first aperture may be positioned within the housing relative to the first light-emitting component according to a first radial offset, the second aperture may be positioned within the housing relative to the second light-emitting component according to a second radial offset, and the first radial offset, the second radial offset, or both, may be based at least in part on the third radial position of the photodetector being offset from the radial midpoint of the segment.

In some examples of the method, apparatuses, and non-transitory computer-readable medium described herein, the first radial offset and the second radial offset comprise radial offsets away from the third radial position of the photodetector.

In some examples of the method, apparatuses, and non-transitory computer-readable medium described herein, the third aperture may be positioned within the housing relative to the photodetector according to a third radial offset based at least in part on third radial position of the photodetector being offset from the radial midpoint of the segment.

In some examples of the method, apparatuses, and non-transitory computer-readable medium described herein, the third radial offset comprises a radial offset toward the second radial position of the second light-emitting component.

In some examples of the method, apparatuses, and non-transitory computer-readable medium described herein, the housing comprises a metal housing.

In some examples of the method, apparatuses, and non-transitory computer-readable medium described herein, the photodetector may be configured to receive light via a first optical path between the first light-emitting component and the photodetector, and via a second optical path between the second light-emitting component and the photodetector, the first optical path may be associated with a first penetration depth into a tissue of a user and, the second optical path may be associated with a second penetration depth into the tissue of the user, and a difference between the first penetration depth and the second penetration depth may be based at least in part on the third radial position of the photodetector being offset from the radial midpoint of the segment.

In some examples of the method, apparatuses, and non-transitory computer-readable medium described herein, a first light-emitting diode configured to emit light within the first wavelength range, a second light-emitting diode configured to emit light within a second wavelength range different from the first wavelength range, and a third light-emitting diode configured to emit light within a third wavelength range different from the first wavelength range and the second wavelength range.

In some examples of the method, apparatuses, and non-transitory computer-readable medium described herein, each of the first wavelength range, the second wavelength range, and the third wavelength range may be associated with one of red light, green light, and infrared light.

In some examples of the method, apparatuses, and non-transitory computer-readable medium described herein, the segment of the inner circumferential surface between the first radial position and the second radial position may be less than 180 degrees.

In some examples of the method, apparatuses, and non-transitory computer-readable medium described herein, a controller communicatively coupled to the first light-emitting component, the second light-emitting component, the photodetector, or any combination thereof, wherein the controller may be configured to and acquire physiological data associated with a user based at least in part on light received by the photodetector, the light emitted by the first light-emitting component, the second light-emitting component, or both.

In some examples of the method, apparatuses, and non-transitory computer-readable medium described herein, selectively activate the first light-emitting component, the second light-emitting component, or both, based at least in part on a first signal quality metric associated with light received by the photodetector via the first optical path, a second signal quality metric associated with light received by the photodetector via the first optical path, a first power consumption associated with the first light-emitting component, a second power consumption associated with the second light-emitting component, or any combination thereof, wherein acquiring the physiological data may be based at least in part on selectively activating the first light-emitting component, the second light-emitting component, or both.

In some examples of the method, apparatuses, and non-transitory computer-readable medium described herein, selectively activate both the first light-emitting component and the second light-emitting component during a first time interval, wherein acquiring the physiological data may be based at least in part on selectively activating the first light-emitting component and the second light-emitting component during the first time interval.

In some examples of the method, apparatuses, and non-transitory computer-readable medium described herein, first light transmitted by the first light-emitting component during the first time interval and received by the photodetector via the first optical path at a second time interval subsequent to the first time interval and second light transmitted by the second light-emitting component during the first time interval and received by the photodetector via the second optical path at a third time interval subsequent to the first time interval and prior to the second time interval, wherein a difference between the second time interval and the third time interval may be based at least in part on a difference between a first length of the first optical path and a second length of the second optical path.

In some examples of the method, apparatuses, and non-transitory computer-readable medium described herein, the physiological data comprises heart rate data and blood oxygen saturation data.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A wearable device, comprising:

a first light-emitting component configured to emit light within at least a first wavelength range, the first light-emitting component positioned within an inner curved surface of the wearable device at a first radial position in a first direction relative to an axis of the wearable device, wherein the axis defines a radial midpoint of the wearable device;

a second light-emitting component configured to emit light within at least the first wavelength range, the second light-emitting component positioned within the inner curved surface of the wearable device at a second radial position in a second direction, opposite the first direction, relative to the axis of the wearable device, wherein the first radial position and the second radial position define a segment of the inner curved surface between the first radial position and the second radial position, and wherein the first radial position and the second radial position are symmetrical across the axis;

a first photodetector configured to receive light emitted by the first light-emitting component via a first optical path associated with a first threshold penetration depth and the second light-emitting component via a second optical path associated with a second threshold penetration depth, different than the first threshold penetration depth, the first photodetector positioned at a third radial position within the segment of the inner curved surface between the first radial position and the second radial position, wherein the third radial position is offset from the axis such that a first radial distance between the first photodetector and the first light-emitting component is greater than a second radial distance between the first photodetector and the second light-emitting component such that the third radial position is asymmetrical across the axis, wherein no additional light-emitting components are positioned between the first photodetector and the first light-emitting component and between the first photodetector and the second light-emitting component;

a second photodetector configured to receive light emitted by the first light-emitting component via a third optical path associated with the second threshold penetration depth and the second light-emitting component via a fourth optical path associated with the first threshold penetration depth, the second photodetector positioned at a fourth radial position outside of the segment of the inner curved surface, wherein the fourth radial position is offset from the axis by a third radial distance and in the first direction; and a third photodetector configured to receive light emitted by the first light-emitting component via a fifth optical path associated with the first threshold penetration depth and the second light-emitting component via a sixth optical path associated with the second threshold penetration depth, the third photodetector positioned at a fifth radial position outside of the segment of the inner curved surface, wherein the fifth radial position is offset from the axis by the third radial distance and in the second direction such that the fourth radial position and the fifth radial position are symmetrical across the axis, wherein the first threshold penetration depth is associated with measurement of a first type of physiological data and the second threshold penetration depth is associated with measurement of a second type of physiological data, different than the first type of physiological data.

2. The wearable device of claim 1, further comprising:
a housing configured to contain at least portions of the first light-emitting component, the second light-emitting component, and the first photodetector;
a first aperture disposed within the inner curved surface of the housing, the first aperture configured to direct light from the first light-emitting component through the housing;
a second aperture disposed within the inner curved surface of the housing, the second aperture configured to direct light from the second light-emitting component through the housing; and
a third aperture disposed within the inner curved surface of the housing, the third aperture configured to direct light through the housing to the first photodetector.

3. The wearable device of claim 2, wherein the first aperture is positioned within the housing relative to the first light-emitting component according to a first radial offset, and wherein the second aperture is positioned within the housing relative to the second light-emitting component according to a second radial offset, wherein the first radial offset, the second radial offset, or both, are based at least in part on the third radial position of the first photodetector being offset from the axis.

4. The wearable device of claim 3, wherein the first radial offset and the second radial offset comprise radial offsets away from the third radial position of the first photodetector.

5. The wearable device of claim 2, wherein the third aperture is positioned within the housing relative to the first photodetector according to a third radial offset based at least in part on the third radial position of the first photodetector being offset from the axis.

6. The wearable device of claim 5, wherein the third radial offset comprises a radial offset toward the second radial position of the second light-emitting component.

7. The wearable device of claim 2, wherein the housing comprises a metal housing.

8. The wearable device of claim 1, wherein the first light-emitting component, the second light-emitting component, or both, comprise:
a first light-emitting diode configured to emit light within the first wavelength range;
a second light-emitting diode configured to emit light within a second wavelength range different from the first wavelength range; and
a third light-emitting diode configured to emit light within a third wavelength range different from the first wavelength range and the second wavelength range.

9. The wearable device of claim 8, wherein each of the first wavelength range, the second wavelength range, and the third wavelength range are associated with one of red light, green light, and infrared light.

10. The wearable device of claim 1, wherein the segment of the inner curved surface between the first radial position and the second radial position is less than 180 degrees.

11. The wearable device of claim 1, further comprising:
a controller communicatively coupled to the first light-emitting component, the second light-emitting component, the first photodetector, or any combination thereof, wherein the controller is configured to:
acquire the first type of physiological data, the second type of physiological data, or both associated with a user based at least in part on light received by the first photodetector, the light emitted by the first light-emitting component, the second light-emitting component, or both.

12. The wearable device of claim 11, wherein the controller is further configured to selectively activate the first light-emitting component, the second light-emitting component, or both, based at least in part on a first signal quality metric associated with light received by the first photodetector via the first optical path, a second signal quality metric associated with light received by the first photodetector via the first optical path, a first power consumption associated with the first light-emitting component, a second power consumption associated with the second light-emitting component, or any combination thereof, wherein acquiring the first type of physiological data, the second type of physiological data, or both is based at least in part on selectively activating the first light-emitting component, the second light-emitting component, or both.

13. The wearable device of claim 11, the controller is further configured to selectively activate both the first light-emitting component and the second light-emitting component during a first time interval, wherein acquiring the first type of physiological data, the second type of physiological data, or both is based at least in part on selectively activating the first light-emitting component and the second light-emitting component during the first time interval.

14. The wearable device of claim 13, wherein the first type of physiological data, the second type of physiological data, or both data is based at least in part on:
first light transmitted by the first light-emitting component during the first time interval and received by the first photodetector via the first optical path at a second time interval subsequent to the first time interval; and
second light transmitted by the second light-emitting component during the first time interval and received by the first photodetector via the second optical path at a third time interval subsequent to the first time interval and prior to the second time interval, wherein a difference between the second time interval and the third time interval is based at least in part on a difference between a first length of the first optical path and a second length of the second optical path.

15. The wearable device of claim 11, wherein the first type of physiological data comprises heart rate data, and wherein the second type of physiological data comprises blood oxygen saturation data.

16. The wearable device of claim 1, wherein the wearable device comprises one of a wearable ring device, a wearable necklace device, a wearable bracelet device, or a wearable anklet device.

17. The wearable device of claim 1, further comprising:
a controller communicatively coupled to the first light-emitting component, the second light-emitting component, the first photodetector, the second photodetector, the third photodetector, or any combination thereof, wherein the controller is configured to:
acquire, at a first time, the first type of physiological data associated with a user based at least in part on light received in accordance with the first threshold penetration depth; and
acquire, at a second time different than the first time, the second type of physiological data associated with the user based at least in part on light received in accordance with the second threshold penetration depth.

* * * * *